(12) United States Patent
Hjort et al.

(10) Patent No.: US 7,172,887 B2
(45) Date of Patent: Feb. 6, 2007

(54) METHODS FOR PRODUCING CITRIC ACID USING HOST CELLS DEFICIENT IN OXALOACETATE HYDROLASE

(75) Inventors: Carsten Mailand Hjort, Smorum (DK); Henrik Pedersen, Albertslund (DK)

(73) Assignee: Novozymes A/S, Bagsvaerd (DK)

( * ) Notice: Subject to any disclaimer, the term of this patent is extended or adjusted under 35 U.S.C. 154(b) by 10 days.

(21) Appl. No.: 11/122,506

(22) Filed: May 4, 2005

(65) Prior Publication Data

US 2005/0202502 A1  Sep. 15, 2005

Related U.S. Application Data

(62) Division of application No. 10/336,491, filed on Jan. 3, 2003, now Pat. No. 6,936,438, which is a division of application No. 09/501,612, filed on Feb. 10, 2000, now Pat. No. 6,544,765.

(60) Provisional application No. 60/121,481, filed on Feb. 24, 1999.

(30) Foreign Application Priority Data

Feb. 22, 1999 (DK) ............................... 1999 00231

(51) Int. Cl.
*C12P 7/48* (2006.01)
*C12N 15/63* (2006.01)
*C12N 1/15* (2006.01)

(52) U.S. Cl. .................... 435/144; 435/455; 435/254.1
(58) Field of Classification Search .................... None
See application file for complete search history.

(56) References Cited

FOREIGN PATENT DOCUMENTS

RU  2089615  9/1997

OTHER PUBLICATIONS

Brown et al, Exploring the new world of the genome with DNA microarrays. Nat Genet. Jan. 1999;21(1 Suppl):33-7. Review.*

Sigma, Inc. Catalogue 1997 Diagnostic Kit for Oxalate pp. 2455.*
Hossain et al, The effect of the sugar source on citric acid production by *Aspergillus niger*. Applied Microbiology & Biotechnology Jun. 1984; 19(6): 393-397.*
Schrickx et al, Organic acid production by *Aspergillus niger* in recycling culture analyzed by capillary electrophoresis.Anal Biochem. Oct. 10, 1995;231(1):175-81.*
Ruijter et al., Oxalic acid production by *Apergillus niger*, Microbiology, vol. 145, pp. 2569-2576 (1999).
Lenz et al., Partial Purification and Some Properties of Oxalacetase from *Aspergillus niger*, Eur. J. Biochem, vol. 65, pp. 225-236 (1976).
Balmforth et al., Isolation and characterization of glyoxylate dehydrogenase from the fungus *Sclerotium rolfsii*, Biochem. J., vol. 218, pp. 113-118 (1984).
William B. A. et al, EMBL, Database Genbank, Acc. No. T82752 (Mar. 15, 1995).
Golubtsova et al., Changes in the Ratio between Citric and Oxalic Acids in *Aspergillus niger* under the Action of Mutagenic Factors, Mikrobiologiya, vol. XLVIII, Issue 6 (1979) (and a translation thereof) USSR.
Shcherbakova et al., The Variability of *Aspergillus niger*, pp. 432-436, translated from Microbiology, vol. 43, pp. 508-513 (1974).
Kasatkina et al., On Methods of Selecting *Aspergillus niger* Mutants with Altered Capacity to Synthesize Organic Acids, Mikrobiologiya, vol. 94, No. 3, pp. 438-444 (1965).
Kubicek et al., Evidence for a Cytoplasmic Pathway of Oxalate Biosynthesis in *Aspergillus niger*, Applied and Environmental Microbiology, vol. 54, pp. 633-637 (1988).
Van Den Hombergh, J. et al., Aspergillus As a Host For Heterologous Protein, Trends in Biotechnology, vol. 15, part 7, pp. 256-263 (1997).
Schrickx et al., Organic Acid Production by *Aspergillus niger*, Analytical Biochemistry, vol. 231, pp. 175-181 (1995).

* cited by examiner

*Primary Examiner*—Sheridan Swope
(74) *Attorney, Agent, or Firm*—Elias J. Lambiris

(57) ABSTRACT

The present invention relates to isolated nucleic acid sequences encoding polypeptides having oxaloacetate hydrolase activity. The invention also relates to nucleic acid constructs, vectors, and host cells comprising the nucleic acid sequences as well as recombinant methods for producing the polypeptides.

15 Claims, 2 Drawing Sheets

Restriction map of the *Aspergillus niger* pyrG plasmid pJRoy 10. The *A. niger* insert and the coding part of the insert are indicated on the figure.

Construction of pHP3

SEQUENCE LISTING

```
<160> NUMBER OF SEQ ID NOS: 33

<210> SEQ ID NO 1
<211> LENGTH: 3494
<212> TYPE: DNA
<213> ORGANISM: Aspergillus niger
<220> FEATURE:
<221> NAME/KEY: Misc_feature
<222> LOCATION: (3370)..(3370)
<223> OTHER INFORMATION: n denotes a, g, c, or t
<220> FEATURE:
<221> NAME/KEY: CDS
<222> LOCATION: (1157)..(1411)
<223> OTHER INFORMATION:
<220> FEATURE:
<221> NAME/KEY: Intron
<222> LOCATION: (1412)..(1503)
<223> OTHER INFORMATION:
<220> FEATURE:
<221> NAME/KEY: CDS
<222> LOCATION: (1504)..(1651)
<223> OTHER INFORMATION:
<220> FEATURE:
<221> NAME/KEY: Intron
<222> LOCATION: (1652)..(1763)
<223> OTHER INFORMATION:
<220> FEATURE:
<221> NAME/KEY: CDS
<222> LOCATION: (1764)..(2383)
<223> OTHER INFORMATION:
```

<400> SEQUENCE: 1

```
tgctccctcg gccaagcgcc aataacgtcc gattcatccc attcctcgtc cagctggcga       60
actccggagg ttgattgctc gctcgctctc agttggccac caaacttact cgtccccctc      120
cttcaccctc cctcctctgc caatgctaca gagtacttgg ctaggctact atcttctcag      180
ctgggtgaag aacaacgggc cccgtgcgtg atgagcaaaa gcgtctgaca tgcagcaact      240
gcagtatact ggagcccgcg gctaccgagg aactcgtgct cgtgtgccac cacatcgaag      300
tgagttgatg cgtcttgtcc atgcagtgtc ggcgtggcct aaagtacggg ccaaacctgt      360
ctgacttcat cccacactat taccccctcc ctcattctcc cctgattcgg cccaataagg      420
aaatcactta gtcaatcaat cctgccatta ccggcgcgta atctgaaact acgcgcggac      480
tgtctcttac tccctcgcg gtgggcggcc cagccagccc catccttact agatttagcg      540
aattactggt cattagccct gtacgggga ggggcgggaa acaaaaatg cgaataatag       600 aataaattta ataagaaaa agaggggggg gggagcttat ctaggccct gctgcattgc        660 attcggacat ttttcgactt gtcacaggca caaatcatag tccgccgatg gcgtcgattg      720 accatttct tttcttttct cggcgctggg atggtggcca agaaaattga atggcaatgg       780
ttcgttcacc ggagtagggt gtacgtgcat tgtgtggatt gacgatgatt ctcggccaag      840
ggcttgcgtt gcaatcccac caggagggga atgttcaga cagacagaaa gcaaagaag       900 tattggaggg aaaaaaacaa ttcttgaaaa atgatcttct caggtaatga atattggttg      960
ctggcgggct gatcttctcc cgacacgtct atataaactg gtcaccttct ggcccttcct     1020
ttctatctct tccttctcat catcagtctc aaacaagcct ctttctctcc taccttcact     1080
ctccactttc tcctttcgaa agggataaaa ctctcctcct cattctcacc tatatatacc     1140
ttgtgctttt ctcgca atg aaa gtt gat acc ccc gat tct gct tcc acc atc     1192
              Met Lys Val Asp Thr Pro Asp Ser Ala Ser Thr Ile
                    1               5                  10 agc atg acc aac act atc acc atc acc gta gag cag gac ggt atc tat     1240
Ser Met Thr Asn Thr Ile Thr Ile Thr Val Glu Gln Asp Gly Ile Tyr
      15                  20                  25 gag atc aac ggt gcc cgt caa gag ccc gtg gtc aac ctg aac atg gtc     1288
Glu Ile Asn Gly Ala Arg Gln Glu Pro Val Val Asn Leu Asn Met Val
 30                  35                  40 acc ggt gcg agc aaa ctg cgc aag cag ctt cgc gag acc aat gag ttg     1336
Thr Gly Ala Ser Lys Leu Arg Lys Gln Leu Arg Glu Thr Asn Glu Leu
45                  50                  55                  60 ctc gtg tgt cct ggt gtg tac gac ggt ctg tcc gcc cgt att gcc atc     1384
Leu Val Cys Pro Gly Val Tyr Asp Gly Leu Ser Ala Arg Ile Ala Ile
              65                  70                  75 aac ctg ggc ttc aag ggc atg tac atg gtatgttgga ttccttagac            1431
Asn Leu Gly Phe Lys Gly Met Tyr Met
              80                  85 tacctttccc cacagtcaac acttctccgc ttccgcgatg gagaaaaaag atcatactaa     1491
cggaaaggtc ag acc ggc gcc ggt act acc gcg tct aga ctg ggc atg gcc     1542
              Thr Gly Ala Gly Thr Thr Ala Ser Arg Leu Gly Met Ala
                                90                      95 gat ctg ggt cta gcc cac atc tac gac atg aag acc aac gca gag atg     1590
Asp Leu Gly Leu Ala His Ile Tyr Asp Met Lys Thr Asn Ala Glu Met
      100                 105                 110 atc gcg aac ctg gac ccc tac ggt cct ccc ctg atc gca gac atg gac     1638
Ile Ala Asn Leu Asp Pro Tyr Gly Pro Pro Leu Ile Ala Asp Met Asp
115                 120                 125                 130 act ggc tac gga g gtgagaatcc cccatctcca ctgtctgcca agacataatg        1691
Thr Gly Tyr Gly
```

-continued

```
Thr Gly Tyr Gly atctacccgc gccaaaaagc aaaacggcaa tatagaccca gttccccact aacaccaaaa      1751
aaacaaaaat ag gc  ccc ctg atg gtc gcc cgt tcc gtt caa caa tac atc      1801
              Gly Pro Leu Met Val Ala Arg Ser Val Gln Gln Tyr Ile
                       140                 145 caa gcc gga gtc gcg gga ttc cac atc gaa gat cag atc caa aac aag        1849
Gln Ala Gly Val Ala Gly Phe His Ile Glu Asp Gln Ile Gln Asn Lys
        150                 155                 160 cga tgc gga cac ctg gca ggc aag cgc gtc gtc acc atg gac gaa tac        1897
Arg Cys Gly His Leu Ala Gly Lys Arg Val Val Thr Met Asp Glu Tyr
    165                 170                 175 ttg act cgc atc cgc gcc gcc aag ctc acc aag gac cgc ctc cgc agc        1945
Leu Thr Arg Ile Arg Ala Ala Lys Leu Thr Lys Asp Arg Leu Arg Ser
180                 185                 190                 195 gac atc gtg ctg att gcc cgc acc gac gcc ctc cag cag cac ggc tac        1993
Asp Ile Val Leu Ile Ala Arg Thr Asp Ala Leu Gln Gln His Gly Tyr
                200                 205                 210 gac gag tgc att cgc cgc ctt aag gcc gcc cgc gat ctt ggc gcc gat        2041
Asp Glu Cys Ile Arg Arg Leu Lys Ala Ala Arg Asp Leu Gly Ala Asp
            215                 220                 225 gtt ggt ctc ctc gag ggc ttc acc agt aag gag atg gcg agg cgg tgt        2089
Val Gly Leu Leu Glu Gly Phe Thr Ser Lys Glu Met Ala Arg Arg Cys
        230                 235                 240 gtc cag gac ctt gcg cct tgg ccg ctt ctc aac atg gtg gag aac            2137
Val Gln Asp Leu Ala Pro Trp Pro Leu Leu Leu Asn Met Val Glu Asn
    245                 250                 255 ggt gct ggg ccg gtt att tcc gtc gat gag gct agg gaa atg ggc ttc        2185
Gly Ala Gly Pro Val Ile Ser Val Asp Glu Ala Arg Glu Met Gly Phe
260                 265                 270                 275 cgc att atg atc ttc tcg ttc gct tgc att act cct gcc tat atg ggg        2233
Arg Ile Met Ile Phe Ser Phe Ala Cys Ile Thr Pro Ala Tyr Met Gly
                280                 285                 290 att acc gct gct ctg gag agg ctc aag aag gat ggt gtg gtt ggg ttg        2281
Ile Thr Ala Ala Leu Glu Arg Leu Lys Lys Asp Gly Val Val Gly Leu
            295                 300                 305 ccc gag ggg atg ggg ccg aag aag ctg ttt gag gtg tgc gga ttg atg        2329
Pro Glu Gly Met Gly Pro Lys Lys Leu Phe Glu Val Cys Gly Leu Met
        310                 315                 320 gac tcg gtg agg gtt gat acc gag gct ggt gga gat ggg ttt gct aat        2377
Asp Ser Val Arg Val Asp Thr Glu Ala Gly Gly Asp Gly Phe Ala Asn
325                 330                 335 ggt gtt taattctttt cttttttttga ttcttaattc cctggttgtt ttgttgtgaa         2433
Gly Val
340
agtttcttat ttttctggtt tgttttattt cccttctgg taactaattt tgtgtgagaa       2493
agagttgttg agttgggttg aactgcattg gatgggattg atttattttc gggatcaaag      2553
tgaaaggaag ggaagggggc tgtgttattg gttttcgagt ggggaccgat atattcctac      2613
tatacatatc gaagcttgcg tggtacatat actagtatct actacattac caagaatgga     2673
aatgaaaact gggtgttaga tttcagttga caggtcttat gttcgtttac cgatagagta     2733
attcctgctt ctcactccat gtgagcccaa tcacaatgga attgtaatct ggttgcctta     2793
taagtactta gtactctgta ctctgtacta cttctcgcat cacatcaaat cttaatactt     2853
agtacgtagt ttgtttcacc cagcaaaacc ttattgcctt aacaatcata ttctcagtaa     2913
gcacgagaca cagaaacgag agaagtattc tagaccctga cagaacwccc tgatcgacag     2973
tcacttaccc aacaaagtaa gtggtctcta ccctctgatt acagttaagg caggcagtag     3033
```

-continued

```
taagcaagaa gaagaaagaa agaataatta actactaagt ttctcactac tgcatgcacg    3093
accacggagt cgccgtgcaa aaaaattggt gcgtgctcag ctagctgcac tctgcacact    3153
gccaccctcg ccctacaaaa gaaaccatgc tgtttctcca ctatactgtt cccgcgatga    3213
aactagggcc aataaccatg cagttactat tggtcccact ggggtgggtt gggtagcctt    3273
atggtattaa aaggagtagg ggtctttgtc gatcgttttc tgttttcttt ttgkattttt    3333
atttytgttg gwctctgttt gtgttgtgtt gggccgnttt tgttttcttt gggtaacgag    3393
ggatgggaat atattcatat ggaaatggaa atggattatg ctattgattg atgaatggtg    3453
atgatctgcg tggaaattaa tgtcagagtc ttgmtgattc a                        3494
```

<210> SEQ ID NO 2
<211> LENGTH: 341
<212> TYPE: PRT
<213> ORGANISM: Aspergillus niger

<400> SEQUENCE: 2

```
Met Lys Val Asp Thr Pro Asp Ser Ala Ser Thr Ile Ser Met Thr Asn
1               5                   10                  15

Thr Ile Thr Ile Thr Val Glu Gln Asp Gly Ile Tyr Glu Ile Asn Gly
            20                  25                  30

Ala Arg Gln Glu Pro Val Val Asn Leu Asn Met Val Thr Gly Ala Ser
        35                  40                  45

Lys Leu Arg Lys Gln Leu Arg Glu Thr Asn Glu Leu Leu Val Cys Pro
    50                  55                  60

Gly Val Tyr Asp Gly Leu Ser Ala Arg Ile Ala Ile Asn Leu Gly Phe
65                  70                  75                  80

Lys Gly Met Tyr Met Thr Gly Ala Gly Thr Thr Ala Ser Arg Leu Gly
                85                  90                  95

Met Ala Asp Leu Gly Leu Ala His Ile Tyr Asp Met Lys Thr Asn Ala
            100                 105                 110

Glu Met Ile Ala Asn Leu Asp Pro Tyr Gly Pro Pro Leu Ile Ala Asp
        115                 120                 125

Met Asp Thr Gly Tyr Gly Gly Pro Leu Met Val Ala Arg Ser Val Gln
    130                 135                 140

Gln Tyr Ile Gln Ala Gly Val Ala Gly Phe His Ile Glu Asp Gln Ile
145                 150                 155                 160

Gln Asn Lys Arg Cys Gly His Leu Ala Gly Lys Arg Val Val Thr Met
                165                 170                 175

Asp Glu Tyr Leu Thr Arg Ile Arg Ala Ala Lys Leu Thr Lys Asp Arg
            180                 185                 190

Leu Arg Ser Asp Ile Val Leu Ile Ala Arg Thr Asp Ala Leu Gln Gln
        195                 200                 205

His Gly Tyr Asp Glu Cys Ile Arg Arg Leu Lys Ala Ala Arg Asp Leu
    210                 215                 220

Gly Ala Asp Val Gly Leu Leu Glu Gly Phe Thr Ser Lys Glu Met Ala
225                 230                 235                 240

Arg Arg Cys Val Gln Asp Leu Ala Pro Trp Pro Leu Leu Leu Asn Met
                245                 250                 255

Val Glu Asn Gly Ala Gly Pro Val Ile Ser Val Asp Glu Ala Arg Glu
            260                 265                 270

Met Gly Phe Arg Ile Met Ile Phe Ser Phe Ala Cys Ile Thr Pro Ala
        275                 280                 285

Tyr Met Gly Ile Thr Ala Ala Leu Glu Arg Leu Lys Lys Asp Gly Val
```

-continued

```
             290                 295                 300
Val Gly Leu Pro Glu Gly Met Gly Pro Lys Lys Leu Phe Glu Val Cys
305                 310                 315                 320

Gly Leu Met Asp Ser Val Arg Val Asp Thr Glu Ala Gly Gly Asp Gly
                325                 330                 335

Phe Ala Asn Gly Val
            340

<210> SEQ ID NO 3
<211> LENGTH: 16
<212> TYPE: PRT
<213> ORGANISM: Aspergillus niger

<400> SEQUENCE: 3

Met Lys Val Asp Thr Pro Asp Ser Ala Ser Thr Ile Ser Met Thr Asn
1               5                   10                  15

<210> SEQ ID NO 4
<211> LENGTH: 15
<212> TYPE: PRT
<213> ORGANISM: Aspergillus niger

<400> SEQUENCE: 4

Thr Asn Thr Ile Thr Ile Thr Val Glu Gln Asp Gly Ile Tyr Glu
1               5                   10                  15

<210> SEQ ID NO 5
<211> LENGTH: 10
<212> TYPE: PRT
<213> ORGANISM: Aspergillus niger

<400> SEQUENCE: 5

Val Glu Gln Asp Gly Ile Tyr Glu Ile Asn
1               5                   10

<210> SEQ ID NO 6
<211> LENGTH: 15
<212> TYPE: PRT
<213> ORGANISM: Aspergillus niger

<400> SEQUENCE: 6

Gly Ala Arg Gln Glu Pro Val Val Asn Leu Asn Met Val Thr Gly
1               5                   10                  15

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
aaagttgata ccccgattc t                                          21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
atggcaatac ggggacagac c                                         21
```

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
caggaaacag ctatgac                                                        17

<210> SEQ ID NO 10
<211> LENGTH: 16
<212> TYPE: DNA
<213> ORGANISM: Artificial Sequence
<220> FEATURE:
<223> OTHER INFORMATION: Primer

<400> SEQUENCE: 10
gtaaaacgac ggccag                                                         16

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
gacggtctgt cgccgtattg c                                                   21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ggaagcagaa tcgggggtat c                                                   21

<210> SEQ ID NO 13
<211> LENGTH: 28
<212> TYPE: DNA
<213> ORGANISM: Artificial Sequence
<220> FEATURE:
<223> OTHER INFORMATION: Primer

<400> SEQUENCE: 13
gcggccgcgc gccaataacg tccgattc                                            28

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
gcggccgcct acaaatacat tgacctccc                                           29

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
aaagttgata cccccgattc t                                              21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
atggcaatac ggcgacagac c                                              21

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
gacggtctgt cgccgtattg c                                              21

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
ggaagcagaa tcgggggtat c                                              21

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gccggagtcg cgggattcca c                                              21

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ggcggactat gatttgtgcc                                                20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
tgatggtcgc ccgttccgtt                                                20

<210> SEQ ID NO 22

```
<211> LENGTH: 21
<212> TYPE: DNA
<213> ORGANISM: Artificial Sequence
<220> FEATURE:
<223> OTHER INFORMATION: Primer

<400> SEQUENCE: 22
tgccattcaa ttttcttggc c                                         21

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
tgatcttcga tgtggaatcc c                                         21

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
gatggcgtcg attgaccatt t                                         21

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
ggagatgggt ttgctaatgg tgtt                                      24

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
ttagcaaacc catctccacc                                           20

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
cgaattactg gtcattagcc c                                         21

<210> SEQ ID NO 28
<211> LENGTH: 21
<212> TYPE: DNA
<213> ORGANISM: Artificial Sequence
<220> FEATURE:
<223> OTHER INFORMATION: Primer

<400> SEQUENCE: 28
```

```
cgagagaagt attctagacc c                                              21

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
tgactgtcga tcagggtgtt                                                20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
gtgtgcggat tgatggactc                                                20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
caacccaact caacaactct                                                20

<210> SEQ ID NO 32
<211> LENGTH: 28
<212> TYPE: DNA
<213> ORGANISM: Artificial Sequence
<220> FEATURE:
<223> OTHER INFORMATION: Primer

<400> SEQUENCE: 32
gcggccgcgc gccaataacg tccgattc                                       28

<210> SEQ ID NO 33
<211> LENGTH: 29
<212> TYPE: DNA
<213> ORGANISM: Artificial Sequence
<220> FEATURE:
<223> OTHER INFORMATION: Primer

<400> SEQUENCE: 33
gcggccgcct acaaatacat tgacctccc                                      29
```

METHODS FOR PRODUCING CITRIC ACID USING HOST CELLS DEFICIENT IN OXALOACETATE HYDROLASE

CROSS-REFERENCE TO RELATED APPLICATIONS

This application is a division of U.S. application Ser. No. 10/336,491 filed Jan. 3, 2003, now U.S. Pat. No. 6,936,438, which is a division of U.S. application Ser. No. 09/501,612 filed Feb. 10, 2000, now U.S. Pat. No. 6,544,765, which claims priority or the benefit under 35 U.S.C. 119 of Danish application no. PA 1999 00231 filed Feb. 22, 1999 and U.S. provisional application Ser. No. 60/121,481 filed Feb. 24, 1999, the contents of which are fully incorporated herun by reference.

BACKGROUND OF THE INVENTION

1. Field of the Invention

The invention relates to isolated nucleic acid sequences encoding polypeptides having oxaloacetate hydrolase activity. The present invention further relates to mutant host cells, in particular fungal mutant host cells such as cells of the genus *Aspergillus*, deficient in oxaloacetate hydrolase activity and thereby in oxalic acid production. The present invention also relates to the use of the mutant cells for producing desirable compounds, such as polypeptides, primary and secondary metabolites, and to methods of producing such compounds in the mutant cells of the invention. The invention also relates to nucleic acid constructs, vectors, and host cells comprising the nucleic acid sequences as well as recombinant methods for producing the polypeptides having oxaloacetate hydrolase activity.

2. Description of Related Art

Filamentous fungi are widely used for the commercial production of a variety of compounds of interest, including homologous compounds, such as primary or secondary metabolites and polypeptides normally produced by the fungus in question or heterologous compounds, such as heterologous polypeptides encoded by foreign DNA which has been introduced into the fungus in question. Such products are produced by fermentation of the fungus in question and harvest of the desired product resulting from the fermentation.

The fungal species *A. niger* is widely used for the commercial production of desired compounds, e.g., citric acid and industrial enzymes. It is well-known that this species produces large amounts of oxalic acid. For a number of reasons the production of oxalic acid is undesirably when this species is used for commercial production of a compound of interest. For instance, the production of oxalic acid requires a lot of carbon and thus extra, expensive carbon sources must be added to the fermentation medium compared to what would be required only for the production of the desired compound; the presence of oxalic acid in the fermentation broth causes problems in the downstream processing involved in the recovery of the product of interest because oxalic acid forms a precipitate with calcium which interferes in the recovery; and oxalic acid is a toxic compound which means that its presence is considered a major problem in the production of food grade products from *A. niger*.

Two possible routes for the pathway for biosynthesis of oxalic acid in *A. niger* have been suggested. The first route is oxaloacetate+water→Oxalic acid+acetate, the reaction being catalyzed by oxaloacetate hydrolase (Kubicek, C. P., G. Schreferl-Kunar, W. Wöhrer and M. Röhr, *Appl. Environ. Microbiol.* 54: 633–637 (1988)). The second route involves the glycoxylate pathway (Balmforth, A. J., A. Thomson, *Biochem. J.* 218: 113–118 (1984)).

It has been attempted to control the formation of oxalic acid during commercial *A. niger* fermentations by conducting the fermentation at a low pH where only little oxalic acid is formed. However, fermentation at low pH may be undesirable since normally this pH is not optimal for the growth of *A. niger* and yield of a desired fermentation product.

A partially purified oxaloacetate hydrolase from *A. niger* has been described (Lenz et al., Partial purification and some properties of oxaloacetate from *Aspergillus niger, Eur. J. Biochem.* 65: 225–236 (1976)), but the gene encoding this enzyme has not been described.

It is an object of the present invention to provide mutants of cells, such as filamentous fungal cells, in particular cells of *A. niger*, which is deficient in oxaloacetate hydrolase production and thereby oxalic acid production.

SUMMARY OF THE INVENTION

The present invention relates to isolated nucleic acid sequences encoding polypeptides having oxaloacetate hydrolase activity, selected from the group consisting of:

(a) a nucleic acid sequence encoding a polypeptide having an amino acid sequence which has at least 65% identity with the amino acid sequence of the oxaloacetate hydrolase of SEQ ID NO: 2;

(b) a nucleic acid sequence having at least 65% homology with the coding part of the DNA sequence SEQ ID NO: 1 (constituted by nucleotides 1157–1411, 1504–1651 and 1764–2383 of SEQ ID NO: 1);

(c) a nucleic acid sequence which hybridizes under medium stringency conditions with (i) the nucleic acid sequence of SEQ ID NO: 1, (ii) the cDNA sequence of SEQ ID NO: 1, (iii) a subsequence of (i) or (ii) of at least 100 nucleotides, or (iv) a complementary strand of (i), (ii), or (iii);

(d) an allelic variant of (a), (b), or (c); and (e) a subsequence of (a), (b), (c), or (d), wherein the subsequence encodes a polypeptide fragment which has oxaloacetate hydrolase activity.

In a further important aspect the invention relates to a method for producing a mutant of a cell, which comprises disrupting or deleting the nucleic acid sequence of the invention or a control sequence thereof, which results in the mutant producing less of the oxaloacetate hydrolase and thus oxalic acid than the cell. The present invention also relates to a mutant produced by this method.

The present invention also relates to nucleic acid constructs, vectors, and host cells comprising the nucleic acid sequences as well as recombinant methods for producing the polypeptides.

DETAILED DESCRIPTION OF THE INVENTION

Figure 1:
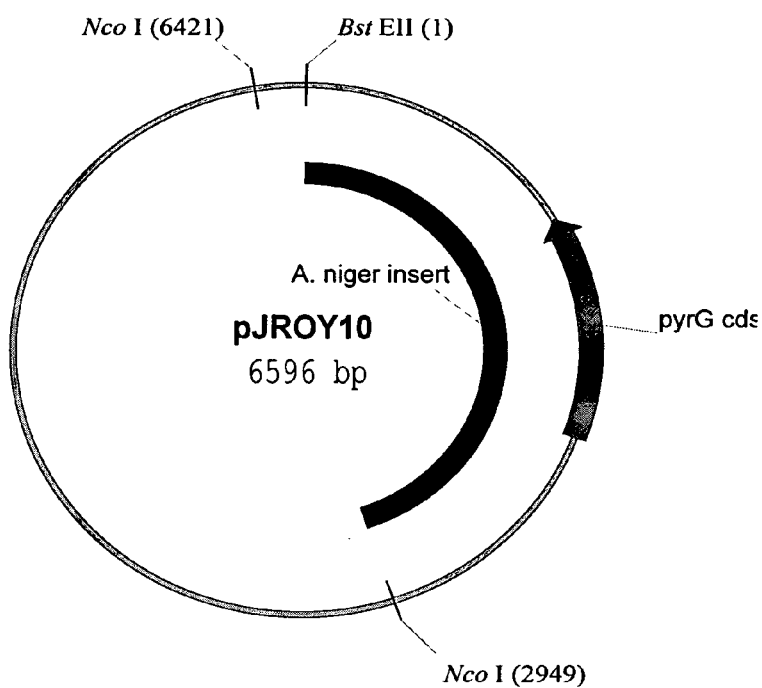
FIG. 1 shows the restriction map of *Aspergillus niger pyrG* plasmid pJRoy10.

Isolated Nucleic Acid Sequences Encoding Polypeptides Having Oxaloacetate Hydrolase Activity The term "oxaloacetate hydrolase activity" is defined herein as an activity which catalyzes the reaction: oxaloacetate+water→Oxalic acid+acetate. The enzyme is classified as belonging to EC 3.7.1.1. For purposes of the present invention, oxaloacetate hydrolase activity is determined according to the procedure described in the Materials and Methods section further below. One unit of oxaloacetate hydrolase activity is defined as 1.0 µmole of oxalic acid produced per minute at 30° C., pH 7.5.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

In a first embodiment, the present invention relates to isolated nucleic acid sequences encoding polypeptides having an amino acid sequence which has a degree of identity to amino acids 1 to 341 of SEQ ID NO: 2 (i.e., the mature polypeptide) of at least about 65%, preferably at least about 70%, more preferably at least about 80%, even more preferably at least about 90%, most preferably at least about 95%, and even most preferably at least about 97%, which have oxaloacetate hydrolase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 1 to 341 of SEQ ID NO: 2. For purposes of the present invention, the degree of identity between two amino acid sequences is determined by the Clustal method (Higgins, *CABIOS* 5: 151–153 (1989)) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=1, gap penalty=3, windows=5, and diagonals=5.

Preferably, the nucleic acid sequences of the present invention encode polypeptides that comprise or consist of the amino acid sequence of SEQ ID NO: 2 or an allelic variant thereof; or a fragment thereof that has oxaloacetate hydrolase activity.

The present invention also encompasses nucleic acid sequences which encode a polypeptide having the amino acid sequence of SEQ ID NO: 2, which differ from SEQ ID NO: 1 by virtue of the degeneracy of the genetic code. The present invention also relates to subsequences of SEQ ID NO: 1 which encode fragments of SEQ ID NO: 2 which have oxaloacetate hydrolase activity or which are sufficiently long to be used for inactivation of an oxaloacetate hydrolase gene in a microbial cell (as described in the section entitled "Removal or Reduction of Oxaloacetate Hydrolase Activity").

A subsequence of SEQ ID NO: 1 is a nucleic acid sequence encompassed by SEQ ID NO: 1 except that one or more nucleotides from the 5' and/or 3' end have been deleted. Preferably, a subsequence contains at least 2800 nucleotides, more preferably at least 3000 nucleotides, and most preferably at least 3200 nucleotides. A fragment of SEQ ID NO: 2 is a polypeptide having one or more amino acids deleted from the amino and/or carboxy terminus of this amino acid sequence. Preferably, a fragment contains at least 270 amino acid residues, more preferably at least 300 amino acid residues, and most preferably at least 320 amino acid residues.

An allelic variant denotes any of two or more alternative forms of a gene occupying the same chomosomal locus. Allelic variation arises naturally through mutation, and may result in polymorphism within populations. Gene mutations can be silent (no change in the encoded polypeptide) or may encode polypeptides having altered amino acid sequences. The allelic variant of a polypeptide is a polypeptide encoded by an allelic variant of a gene.

The amino acid sequences of the homologous polypeptides may differ from the amino acid sequence of SEQ ID NO: 2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a second embodiment, the present invention relates to isolated nucleic acid sequences which have a degree of homology to the mature polypeptide coding sequence of SEQ ID NO: 1 (constituted by nucleotides 1157–1411, 1504–1651 and 1764–2383 of SEQ ID NO: 1) of at least about 65%, preferably about 70%, preferably about 80%, more preferably about 90%, even more preferably about 95%, and most preferably about 97% homology, which encode an active polypeptide or which are sufficiently long to be used for inactivation of an oxaloacetate hydrolase gene in a microbial cell (as described in the section entitled "Removal or Reduction of Oxalolacetate Hydrolase Activity"); or allelic variants and subsequences of SEQ ID NO: 1 which encode polypeptide fragments which have oxaloacetate hydrolase activity or which are sufficiently long to be used for inactivation of an oxaloacetate hydrolase gene in a microbial cell (as described in the section entitled "Removal or Reduction of Oxaloacetate Hydrolase Activity"). For purposes of the present invention, the degree of homology between two nucleic acid sequences is determined by the computer program Align provided in the Fasta program package (Version v20u6), using GAP with the following settings for nucleotide sequence comparison: GAP creation penalty (for the first residue) in a GAP of −16 and GAP extension (for the additional residues) penalty of −4. Align is a slightly modified version of a program taken from E. Myers and W. Miller. The algorithm is described in E. Myers and W. Miller, "Optimal Alignments in Linear Space" (*CABIOS* 4: 11–17 (1988)).

In a third embodiment, the present invention relates to isolated nucleic acid sequences encoding polypeptides having oxaloacetate hydrolase activity which hybridize under medium stringency conditions, more preferably medium-high stringency conditions, even more preferably high stringency conditions, and most preferably very high stringency conditions with a nucleic acid probe which hybridizes under the same conditions with (i) the nucleic acid sequence of SEQ ID NO: 1, (ii) the cDNA sequence of SEQ ID NO: 1, (iii) a subsequence of (i) or (ii), or (iv) a complementary strand of (i), (ii), or (iii) (J. Sambrook, E. F. Fritsch, and T. Maniatus, Molecular Cloning, A Laboratory Manual, 2d edition, Cold Spring Harbor, N.Y. (1988)). The subsequence of SEQ ID NO: 1 may be at least 100 nucleotides or preferably at least 200 nucleotides. Moreover, the subsequence may encode a polypeptide fragment which has oxaloacetate hydrolase activity.

The nucleic acid sequence of SEQ ID NO: 1 or a subsequence thereof, as well as the amino acid sequence of SEQ ID NO: 2 or a fragment thereof, may be used to design a nucleic acid probe to identify and clone DNA encoding polypeptides having oxaloacetate hydrolase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA which hybridizes with the probes described above and which encodes a polypeptide having oxaloacetate hydrolase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1 or a subsequence thereof, the carrier material is used in a Southern blot. For purposes of the present invention, hybridization indicates that the nucleic acid sequence hybridizes to a nucleic acid probe corresponding to the nucleic acid sequence shown in SEQ ID NO: 1, its complementary strand, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO: 2, or a subsequence thereof. In another preferred embodiment, the nucleic acid probe is SEQ ID NO: 1. In another preferred embodiment, the nucleic acid probe is the nucleotides encoding the fragment of SEQ ID NO: 2 constituted by amino acid residues 123–205 or a part of this fragment. In another preferred embodiment, the nucleic acid probe is the nucleic acid sequence contained in plasmid pHP1 which is contained in *Escherichia coli* DSM-12660 wherein the nucleic acid sequence encodes a polypeptide having oxaloacetate hydrolase activity, in particular the mature polypeptide coding region of SEQ ID NO: 1.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (Proceedings of the National Academy of Sciences U.S.A., 48: 1390 (1962)) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

The present invention also relates to isolated nucleic acid sequences produced by (a) hybridizing a DNA under medium, medium-high, high, or very high stringency conditions with the sequence of SEQ ID NO: 1, or its complementary strand, or a subsequence thereof; and (b) isolating the nucleic acid sequence. The subsequence is preferably a sequence of at least 100 nucleotides such as a sequence which encodes a polypeptide fragment which has oxaloacetate hydrolase activity or a sequence which is sufficiently long to be used for inactivation of an oxaloacetate hydrolase gene in a microbial cell (as described in the section entitled "Removal or Reduction of Oxaloacetate Hydrolase Activity").

The polypeptides encoded by the isolated nucleic acid sequences of the present invention have at least 20%, preferably at least 40%, more preferably at least 60%, even more preferably at least 80%, even more preferably at least 90%, and most preferably at least 100% of the oxaloacetate hydrolase activity of the mature polypeptide of SEQ ID NO: 2.

The nucleic acid sequences of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted.

The nucleic acid sequences may be obtained from a bacterial source. For example, these polypeptides may be obtained from a gram positive bacterium such as a *Bacillus* strain, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis*; or a *Streptomyces* strain, e.g., *Streptomyces lividans* or *Streptomyces murinus*; or from a gram negative bacterium, e.g., *E. coli* or *Pseudomonas* sp.

In a preferred embodiment, the nucleic acid sequence is obtained from a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, CAB International, University Press, Cambridge, UK (1995)) as well as the Oomycota (as cited in Hawksworth et al., supra, page 171 (1995)) and all mitosporic fungi (Hawksworth et al., 1995, supra).

In a more preferred embodiment, the fungal cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, (1980)).

More specifically, the nucleic acid sequences may be obtained from a yeast strain such as a *Candida, Hansenula, Kluyveromyces, Pichia, Saccharomyces, Schizosaccharomyces,* or *Yarrowia* strain; or more preferably from a filamentous fungal strain such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma* strain.

In a preferred embodiment, the nucleic acid sequences are obtained from a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* strain.

In another preferred embodiment, the nucleic acid sequences are obtained from an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* strain.

In a more preferred embodiment, the nucleic acid sequences are obtained from *Aspergillus niger*, and most preferably from *A. niger* BO1 DSM 12665, e.g., the nucleic acid sequence set forth in SEQ ID NO: 1. In another more preferred embodiment, the nucleic acid sequence is the sequence contained in plasmid pHP1 which is contained in *Escherichia coli* DSM-12660. In another preferred embodiment, the nucleic acid sequence is a nucleotide sequence constituted by nucleotides 1157–1411, 1504–1651 and 1764–2383 of SEQ ID NO: 1, which encodes the mature polypeptide of SEQ ID NO: 2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. For example, the polypeptides may be obtained from microorganisms which are taxonomic equivalents of *Aspergillus niger* as defined by Benn and Klich (Benn J. W. and M. A. Klich, *Aspergillus*, Biology and industrial applications. Butterworth-Heinemann, U.S.A. (1992)), regardless of the species name by which they are known, e.g., *A. aculeatus, A. awamori, A. carboniarus, A. ellipticus, A. ficuum, A. foetidus, A. heteromorphus, A. japonicus, A. phoenicis, A. pulverulentus, A. tubingensis, A. helicothrix, A. atroviolaceus, A. citricus, A. acidicus* or *A. fonsecaeus.*

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such nucleic acid sequences may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., PCR: A Guide to Methods and Application, Academic Press, New York (1990). For PCR it may be of particular relevance to use a set of primers spanning the nucleotide sequence encoding amino acids 123–205 of SEQ ID NO: 2. Other nucleic acid amplification procedures such as ligase chain reaction (LCR), ligated activated transcription (LAT) and nucleic acid sequence-based amplification (NASBA) may be used. The nucleic acid sequence may be cloned from a strain of *Aspergillus*, or another or related organism and thus, for example, may be an allelic or species variant of the polypeptide encoding region of the nucleic acid sequence.

Modification of a nucleic acid sequence of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO: 1, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., *Protein Expression and Purification* 2: 95–107 (1991).

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, *Science* 244: 1081–1085 (1989)). In the latter technique, mutations are introduced at every positively charged residue in the molecule, and the resultant mutant molecules are tested for oxaloacetate hydrolase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., *Science* 255: 306–312 (1992); Smith et al., *Journal of Molecular Biology* 224: 899–904 (1992); Wlodaver et al., *FEBS Letters* 309: 59–64 (1992)).

Methods for Producing Mutant Nucleic Acid Sequences

The present invention further relates to methods for producing a mutant nucleic acid sequence, comprising introducing at least one mutation into the mature polypeptide coding sequence of SEQ ID NO: 1 or a subsequence thereof, wherein the mutant nucleic acid sequence encodes a polypeptide which consists of amino acids 1 to 341 of SEQ ID NO: 2 or a fragment thereof which has oxaloacetate hydrolase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Removal or Reduction of Oxaloacetate Hydrolase Activity

The present invention also relates to methods for producing a mutant cell of a parent cell, which comprises disrupting or deleting a nucleic acid sequence of the present invention or a control sequence thereof, which results in the mutant cell producing less of the polypeptide having oxaloacetate hydrolase activity encoded by the nucleic acid sequence than the parent cell and thus less oxalic acid when cultivated under the same conditions.

The construction of strains that have reduced oxaloacetate hydrolase activity and oxalic acid production may be conveniently accomplished by modification or inactivation of a nucleic acid sequence necessary for expression of the polypeptide having oxaloacetate hydrolase activity in the cell. The nucleic acid sequence to be modified or inactivated may be, for example, a nucleic acid sequence encoding the polypeptide or a part thereof essential for exhibiting oxaloacetate hydrolase activity, e.g., a nucleic acid sequence of the invention as described in the section entitled "Isolated Nucleic Acid Sequences Encoding Polypeptides Having Oxaloactate Hydrolase Activity", or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification are described further in this section.

Modification or inactivation of the nucleic acid sequence may be performed by subjecting the cell to mutagenesis and selecting or screening for cells in which the oxaloacetate hydrolase producing capability has been reduced. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced oxaloacetate hydrolase activity or production. The reduced or eliminated oxaloacetate hydrolase activity may be determined by use of the assay described in the Examples below.

Modification or inactivation of production of a polypeptide encoded by a nucleic acid sequence of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleic acid sequence to be modified, it is preferred that the modification be performed in vitro as exemplified below.

An example of a convenient way to eliminate or reduce production by a host cell of choice is based on techniques of gene replacement or gene interruption. For example, in the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, in particular of any of the species listed in the section above entitled "Isolated Nucleic Acid Sequences Encoding Polypeptides Having Oxaloacetate Hydrolase Activity" as sources for the nucleic acid sequence of the invention encoding a polypeptide with oxaloacetate hydrolase activity. Preferably, the cell is a fungal strain which is suitable for the production of desired products such as polypeptides or primary or secondary metabolites, either homologous or heterologous to the cell. Even more preferably, the cell is a cell of *Aspergillus*, in particular *A. niger*.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous expression products, such as homologous or heterologous polypeptides or primary or secondary metabolites. Therefore, the present invention further relates to methods for producing a homologous or heterologous product comprising (a) cultivating the mutant cell under conditions conducive for production of the product; and (b) recovering the product.

The methods used for cultivation and purification of the product of interest may be performed by methods known in the art, e.g., as described further below in the section entitled "Methods of Production".

The methods of the present invention for producing an essentially oxalic acid free product is of particular interest in the production of primary metabolites, in particular food grade products such as citric acid and other Krebs cyclus acids, and homologous or heterologous polypeptides, in particular eukaryotic polypeptides.

The polypeptide may be any polypeptide heterologous or homologous to the mutant cell. The term "polypeptide" is not meant herein to refer to a specific length of the encoded product, and therefore, encompasses peptides, oligopeptides, and proteins. The term "heterologous polypeptide" is defined herein as a polypeptide that is not native to the mutant cell, a native (or protein in which modifications have been made to alter the native sequence, or a native protein whose expression is quantitatively altered as a result of a manipulation of the mutant cell by recombinant DNA techniques. The mutant cell may contain one or more copies of the nucleic acid sequence encoding the homologous or heterologous polypeptide. In a preferred embodiment, the heterologous polypeptide is an extracellularly secreted polypeptide.

Preferably, the polypeptide to be produced is a hormone, hormone variant, enzyme, receptor or portion thereof, antibody or portion thereof, or reporter. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The oxaloacetate hydrolase-deficient cells may also be used to express heterologous proteins of pharmaceutical interest such as hormones, growth factors, receptors, and the like.

The nucleic acid sequence encoding a heterologous polypeptide that can be expressed in a mutant cell of the invention, in particular a filamentous fungal mutant cell, may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

In the methods of the present invention, the mutant cell, in particular a mutant filamentous fungal cell may also be used for the recombinant production of polypeptides or other products such as primary or secondary metabolites that are native (or "homologous") to the cell.

The techniques used to isolate or clone a nucleic acid sequence encoding a heterologous polypeptide are known in the art and include isolation from genomic DNA, preparation from cDNA, or a combination thereof. The cloning of the nucleic acid sequence from such genomic DNA can be effected, e.g., by using the well known polymerase chain reaction (PCR). See, for example, Innis et al., PCR Protocols: A Guide to Methods and Application, Academic Press, New York (1990). The cloning procedures may involve excision and isolation of a desired nucleic acid fragment comprising the nucleic acid sequence encoding the polypeptide, insertion of the fragment into a vector molecule, and incorporation of the recombinant vector into the mutant cell where multiple copies or clones of the nucleic acid sequence will be replicated. The nucleic acid sequence may be of genomic, cDNA, RNA, semisynthetic, synthetic origin, or any combinations thereof.

In the methods of the present invention, heterologous polypeptides may also include fused or hybrid polypeptides in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator. The hybrid polypeptides may comprise a combination of partial or complete polypeptide sequences obtained from at least two different polypeptides wherein one or more may be heterologous to the mutant cell.

An isolated nucleic acid sequence encoding a heterologous polypeptide of interest may be manipulated in a variety of ways to provide for expression of the polypeptide. Expression will be understood to include any step involved in the production of the polypeptide including, but not limited to, transcription, post-transcriptional modification, translation, post-translational modification, and secretion. Manipulation of the nucleic acid sequence prior to its insertion into a vector may be desirable or necessary depending on the expression vector. The techniques for modifying nucleic acid sequences utilizing cloning methods are well known in the art.

"Nucleic acid construct" is defined herein as a nucleic acid molecule, either single- or double-stranded, isolated from a naturally occurring gene or modified to contain segments of nucleic acid that are combined and juxtaposed in a manner which would not otherwise exist in nature. The term nucleic acid construct is synonymous with the term expression cassette when the nucleic acid construct contains all the control sequences required for expression of a coding sequence. The term "coding sequence" as defined herein is a sequence that is transcribed into mRNA and translated into a polypeptide. The boundaries of the coding sequence are generally determined by the ATG start codon located just upstream of the open reading frame at the 5' end of the mRNA and a transcription terminator sequence located just downstream of the open reading frame at the 3' end of the mRNA. A coding sequence can include, but is not limited to, genomic, cDNA, RNA, semisynthetic, synthetic, recombinant, or any combinations thereof. The coding sequence of the nucleic acid construct described herein may be the nucleotide sequence of the invention encoding a polypeptide with oxaloacetate activity (as defined in the section above entitled "Isolated Nucleic Acid Sequences Encoding Polypeptides Having Oxaloacetate Hydrolase Activity) in which case the nucleic acid construct is used for producing a polypeptide with oxaloacetate activity as defined in said section or other manipulation involving said nucleic acid sequence; or the coding sequence may be one encoding a heterologous polypeptide to be produced in a mutant cell of the invention.

The term "control sequences" is defined herein to include all components that are necessary or advantageous for the expression of a heterologous polypeptide. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a heterologous polypeptide. The term "operably linked" is defined herein as a configuration in which a control sequence is appropriately placed at a position relative to the coding sequence of the DNA sequence such that the control sequence directs the production of a heterologous polypeptide.

The control sequence may be an appropriate promoter sequence, a nucleic acid sequence that is recognized by a cell, in particular a filamentous fungal cell for expression of the nucleic acid sequence. The promoter sequence contains transcriptional control sequences that mediate the expression of the heterologous polypeptide. The promoter may be any nucleic acid sequence that shows transcriptional activity in the cell including mutant, truncated, and hybrid promoters, and may be obtained from genes encoding extracellular or intracellular polypeptides either homologous or heterologous to the cell.

Examples of suitable promoters for directing the transcription of the nucleic acid constructs in a filamentous fungal cell in the methods of the present invention are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Aspergillus oryzae* acetamidase (amdS), *Fusarium oxysporum* trypsin-like protease (U.S. Pat. No. 4,288,627), and mutant, truncated, and hybrid promoters thereof. Particularly preferred promoters are the NA2-tpi (a hybrid of the promoters from the genes encoding *Aspergillus niger* neutral alpha-amylase and *Aspergillus oryzae* triose phosphate isomerase), glucoamylase, and TAKA amylase promoters.

The control sequence may also be a suitable transcription terminator sequence, a sequence recognized by the host cell in question to terminate transcription. The terminator sequence is operably linked to the 3' terminus of the nucleic acid sequence encoding the heterologous polypeptide. Any terminator that is functional in the host cell may be used in the present invention.

Preferred terminators functional in filamentous fungal cells are obtained from the genes encoding *Aspergillus oryzae* TAKA amylase, *Aspergillus niger* glucoamylase, *Aspergillus nidulans* anthranilate synthetase, *Aspergillus niger* alpha-glucosidase, and *Fusarium oxysporum* trypsin-like protease.

The control sequence may also be a suitable leader sequence, a nontranslated region of a mRNA that is important for translation by the cell. The leader sequence is operably linked to the 5' terminus of the nucleic acid sequence encoding the heterologous polypeptide. Any leader sequence that is functional in the cell may be used in the present invention.

Preferred leaders are obtained from the genes encoding *Aspergillus oryzae* TAKA amylase and *Aspergillus nidulans* triose phosphate isomerase.

The control sequence may also be a polyadenylation sequence, a sequence operably linked to the 3' terminus of the nucleic acid sequence and, when transcribed, is recognized by a cell as a signal to add polyadenosine residues to transcribed mRNA. Any polyadenylation sequence that is functional in the cell may be used in the present invention.

Preferred polyadenylation sequences functional in filamentous fungal cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

The control sequence may also be a signal peptide coding region that codes for an amino acid sequence linked to the amino terminus of the heterologous polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. The signal peptide coding region may be obtained from a glucoamylase or an amylase gene from an *Aspergillus* species, or a lipase or proteinase gene from a *Rhizomucor* species. However, any signal peptide coding region that directs the expressed heterologous polypeptide into the secretory pathway of a cell may be used in the present invention.

An effective signal peptide coding region in a filamentous fungal cell is the signal peptide coding region obtained from the genes encoding *Aspergillus oryzae* TAKA amylase, *Aspergillus niger* neutral amylase, *Rhizomucor miehei* aspartic proteinase gene, and *Humicola lanuginosa* cellulase.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature, active polypeptide by catalytic or autocatalytic cleavage of the propeptide from the propolypeptide. The propeptide coding region may be obtained from the genes encoding *Rhizomucor miehei* aspartic proteinase and *Myceliophthora thermophila* laccase (WO 95/33836).

Where both signal peptide and propeptide regions are present at the amino terminus of a polypeptide, the propeptide region is positioned next to the amino terminus of the polypeptide and the signal peptide region is positioned next to the amino terminus of the propeptide region.

The nucleic acid constructs may also comprise one or more nucleic acid sequences that encode one or more factors that are advantageous for directing the expression of the heterologous polypeptide, e.g., a transcriptional activator (e.g., a trans-acting factor), chaperone, and processing protease. Any factor that is functional in the host cell, in particular in a filamentous fungal cell may be used in the present invention. The nucleic acids encoding one or more of these factors are not necessarily in tandem with the nucleic acid sequence encoding the heterologous polypeptide.

It may also be desirable to add regulatory sequences that allow the regulation of the expression of the heterologous polypeptide relative to the growth of the cell. Examples of regulatory systems are those that cause the expression of the gene to be turned on or off in response to a chemical or physical stimulus, including the presence of a regulatory compound. The TAKA alpha-amylase promoter, *Aspergillus niger* glucoamylase promoter, and *Aspergillus oryzae* glucoamylase promoter may be used as regulatory sequences in filamentous fungal cells. Other examples of regulatory sequences are those that allow for gene amplification, e.g., the metallothionein genes which are amplified with heavy metals. In these cases, the nucleic acid sequence encoding the heterologous polypeptide would be operably linked with the regulatory sequence.

The various nucleic acid and control sequences described above may be joined together to produce a recombinant expression vector that may include one or more convenient restriction sites to allow for insertion or substitution of the nucleic acid sequence encoding the heterologous polypeptide at such sites. Alternatively, the nucleic acid sequence encoding the heterologous polypeptide may be expressed by inserting the sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) that can be conveniently subjected to recombinant DNA procedures and can bring about the expression of the nucleic acid sequence encoding the heterologous polypeptide. The choice of the vector will typically depend on the compatibility of the vector with the cell into which the vector is to be introduced. The vector may be a linear or closed circular plasmid. The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the cell, is integrated into the genome and replicated together with the chromosome(s) into which it has been integrated. The vector system may be a single vector or plasmid or two or more vectors or plasmids that together contain the total DNA to be introduced into the genome of the cell, or a transposon.

The vector preferably contains one or more selectable markers that permit easy selection of transformed cells. A selectable marker is a gene the product of which provides for biocide or viral resistance, resistance to heavy metals, prototrophy to auxotrophs, and the like. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in a filamentous fungal cell are the amdS and pyrG genes of *Aspergillus nidulans* or *Aspergillus oryzae* and the bar gene of *Streptomyces hygroscopicus*.

The vector preferably contains an element(s) that permits stable integration of the vector into a cell genome or autonomous replication of the vector in the cell independent of the genome of the cell.

"Introduction" means introducing a vector comprising the nucleic acid sequence into a cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the chromosome occurs by homologous recombination, non-homologous recombination, or transposition.

The introduction of an expression vector into a cell may involve a process consisting of protoplast formation, transformation of the protoplasts, and regeneration of the cell wall in a manner known per se. Suitable procedures for transformation of *Aspergillus* host cells are described in EP 238 023 and Yelton et al., *Proceedings of the National Academy of Sciences U.S.A.* 81: 1470–1474 (1984). A suitable method of transforming *Fusarium* species is described by Malardier et al., *Gene* 78: 147–156 (1989) or in WO 96/00787.

For integration into the genome of a cell, the vector may rely on the nucleic acid sequence encoding the heterologous polypeptide or any other element of the vector for stable integration of the vector into the genome by homologous or nonhomologous recombination. Alternatively, the vector may contain additional nucleic acid sequences for directing integration by homologous recombination into the genome of the cell. The additional nucleic acid sequences enable the vector to be integrated into the genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequences that are homologous with the target sequence in the genome of the cell. Furthermore, the integrational elements may be non-encoding or encoding nucleic acid sequences. On the other hand, the vector may be integrated into the genome of the cell by non-homologous recombination.

For autonomous replication, the vector may further comprise an origin of replication enabling the vector to replicate autonomously in the filamentous fungal cell in question.

It will be understood that the methods of the present invention are not limited to a particular order for obtaining the mutant cell. The modification of a gene involved in the production of a polypeptide with oxaloacetate hydrolase activity may be introduced into the parent cell at any step in the construction of the cell for the production of a heterologous polypeptide. It is preferable that the cell has already been made oxaloacetate hydrolase-deficient using the methods of the present invention prior to the introduction of a gene encoding a heterologous polypeptide.

The procedures used to ligate the elements described herein to construct the recombinant expression vectors are well known to one skilled in the art (see, e.g., J. Sambrook, E. F. Fritsch, and T. Maniatis, Molecular Cloning, A Laboratory Manual, 2d edition, Cold Spring Harbor, N.Y. (1989)).

The present invention also relates to methods for obtaining oxaloacetate hydrolase-deficient mutant cells, in particular filamentous fungal mutant cells which comprise (a) introducing into a parent cell, in particular a parent filamentous fungal cell a first nucleic acid sequence comprising a modification of at least one of the genes involved in the production of a oxaloacetate hydrolase and a second nucleic acid sequence encoding a heterologous polypeptide; and (b) identifying the mutant from step (a) comprising the modified nucleic acid sequence, wherein the mutant cell produces less of the oxaloacetate hydrolase than the parent cell of the mutant cell when cultured under the same conditions.

The present invention also relates to oxaloacetate hydrolase-deficient mutants of cells, in particular filamentous fungal cells for producing a heterologous polypeptide which comprise a first nucleic acid sequence comprising a modification of at least one of the genes involved in the production of a polypeptide with oxaloacetate hydrolase activity and a second nucleic acid sequence encoding the heterologous polypeptide, wherein the mutant produces less of the polypeptide with oxaloacetate hydrolase activity than the parent cell of the mutant cell when cultured under the same conditions.

In another aspect of the present invention, the mutant cell may additionally contain modifications of one or more nucleic acid sequences which encode proteins that may be detrimental to the production, recovery, and/or application of the desired product such as the heterologous polypeptide of interest. The modification reduces or eliminates expression of the one or more third nucleic acid sequences resulting in a mutant cell with a modified third nucleic acid sequence which may produce more of the heterologous polypeptide than the mutant cell without the modification of the third nucleic acid sequence when cultured under the same conditions. The third nucleic acid sequence may encode any protein or enzyme. For example, the enzyme may be an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, a pectinolytic enzyme, peroxidase, phospholipase, phytase, polyphenoloxidase, proteolytic enzyme, ribonuclease, transglutaminase, and xylanase. The third nucleic acid sequence preferably encodes a proteolytic enzyme, e.g., an aminopeptidase, a carboxypeptidase, or a protease.

In a further aspect, the present invention relates to a protein product essentially free from oxaloacetate hydrolase activity which is produced by a method of the present invention.

The present invention also relates to nucleic acid constructs, recombinant expression vectors, and host cells containing the nucleic acid sequence of SEQ ID NO: 1, subsequences or homologues thereof (as defined in the section entitled "Isolated Nucleic Acid Sequences Encoding Polypeptides Having Oxaloacetate Hydrolase Activity"), for expression of the sequences. The constructs and vectors may be constructed as described herein. The host cell may be any cell suitable for the expression the nucleic acid sequence, in particular any of the cells mentioned in the section entitled "Isolated Nucleic Acid Sequences Encoding Polypeptides Having Oxaloacetate Hydrolase Activity" as a source for the nucleic acid sequences of the invention. In particular, the host cell is a filamentous fungal cell, such as a cell of *Aspergillus*, such as *A. niger* or *A. oryzae* or a cell of *Fusarium*.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., *Proceedings of the National Academy of Sciences U.S.A.* 81: 1470–1474 (1984). Suitable methods for transforming *Fusarium* species are described by Malardier et al., 1989, *Gene* 78: 147–156 and WO 96/00787. Yeast may be transformed using the procedures described by Becker and Guarente, In Abelson, J. N. and Simon, M. I., editors, Guide to Yeast Genetics and Molecular Biology, *Methods in Enzymology* 194: 182–187, Academic Press, Inc., New York; Ito et al., *Journal of Bacteriology* 153: 163 (1983); and Hinnen et al., *Proceedings of the National Academy of Sciences U.S.A.* 75: 1920 (1978).

Methods of Production

The present invention also relates to methods for producing a polypeptide encoded by a nucleotide sequence of the invention comprising (a) cultivating a host cell harboring a nucleotide sequence of the invention under conditions suitable for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the mature polypeptide coding region of SEQ ID NO: 1, wherein the mutant nucleic acid sequence encodes a polypeptide which consists of amino acids 1 to 341 of SEQ ID NO: 2, and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J. -C. Janson and Lars Ryden, editors, VCH Publishers, New York (1989)).

Uses

The present invention is also directed to methods of using the polypeptides having oxaloacetate hydrolase activity.

The polypeptides of the present invention may be used as a diagnostic enzyme, e.g., for the detection of oxalic acid in food or other products.

The nucleotide sequences of the present invention may be used for modification of the production of oxaloacetate hydrolase and thus oxalic by a cell, such as a microbial cell normally producing the hydrolase. In particular, the nucleotide sequences may be used to reduce or eliminate oxaloacetate hydrolase and thus oxalic acid production of the cell in question.

The present invention is further described by the following examples which should not be construed as limiting the scope of the invention.

EXAMPLES

Chemicals used as buffers and substrates were commercial products of at least reagent grade.

Strains:
Aspergillus niger BO 1 (DSM 12665)
Escherichia coli DH 5α D. M. Woodcock et al., Nucleic Acids Res. 17: 3469–3478 (1989)

Media and Assays
Buffer A: 50 mM Tris/HCl pH 7.5, 2 mM $MnCl_2$, 20 mM DTT, 5% sucrose.
Oxaloacetate hydrolase activity assay: 1000 ml 0.1 M MOPS, pH 7.5, 2 mM $MnCl_2$, 25 ml 40 mM oxaloacetate, 5 to 100 ml sample. The absorbance was measured at 255 nm. The activity was determined from the rate of decrease in absorbance and the absorption coefficient of oxaloacetate (1.1 $mM^{-1}$ $cm^{-1}$, Lenz et al, Partial purification and some properties of oxalacetase from Aspergillus niger, Eur. J. Biochem. 65: 225–236 (1976)). The assay was carried out at 30° C.

Protein assay: Protein concentrations were measured by using the BioRad (Hercules, Calif., U.S.A.) Bio-Rad Protein Assay) cat. No. 500-0006 following the manufacturer's instructions and with bovine serum albumine as a standard.

Example 1

Purification of the Oxaloacetate Hydrolase (EC 3.7.1.1)

Aspergillus niger BO1 was fermented in shake flasks at 30° C. in the medium: sucrose 20 g/L, $NaNO_3$ 15 g/L, $KH_2PO_4$ 1.5 g/L, $MgSO_4$, $7H_2O$ 1 g/L, NaCl 1 g/L, $CaCl_2$, $2H_2O$ 0.1 g/L, trace solution 0.5 ml/L. Trace solution: $ZnSO_4$, $7H_2O$ 14.3 g/L, $CuSO_4$, $5H_2O$ 2.5 g/L, $NiCl_2$, $6H_2O$ 0.5 g/L, $FeSO_4$, $7H_2O$ 13.8 g/L, $MnCl_2$ 6 g/L. The pH was 2.5 until a biomass concentration of about 0.5 g/L was reached. Then the pH was shifted to 6 by addition of 2 M NaOH and the cells were grown until the biomass concentration reached about 5 g/L. The cells were harvested by filtration, washed with 0.9% (w/v) NaCl and then frozen in liquid nitrogen. The frozen cells were disrupted in a morter under liquid nitrogen and then suspended in buffer A. The suspension was centrifuged (15 min, 40.000×g, 4° C.), and the supernatant was isolated. Ammoniumsulphate was added to 45% saturation (277 g/l), and the formed suspension was centrifuged (15 min, 40.000×g, 4° C.), and the supernatant was discharged. The pellet was dissolved in buffer A and filtered through a 0.45 micro-m filter.

Ammonium sulfate was added to the sample to a conductivity of 50 mS/cm. The sample was then applied onto a Phenyl Sepharose High Performance column (Amersham Pharmacia Biotech, Uppsala) equilibrated with 0.5 M ammonuim sulfate dissolved in buffer A, following the manufacturer's instructions. The column was washed with the same buffer and then eluted using a linear salt gradient from 0.5 M Ammonium sulfate dissolved in buffer A to pure buffer A.

Fractions having oxaloacetate hydrolase activity were pooled. This solution was diluted with 2 mM $MnCl_2$, 20 mM DTT, 5% sucrose to a conductivity of 4 mS/cm and then applied to a Q sepharose High Performance column (Amersham Pharmacia Biotech, Uppsala) equilibrated with buffer A. The column was washed with buffer A and then eluted using a linear salt gradient from 0 M to 0.5 M NaCl dissolved in buffer A. Fractions having oxaloacetate hydrolase activity were pooled.

The samples were applied to PD-10 columns (Amersham Pharmacia Biotech, Uppsala) equilibrated with 10 mM $NaH_2PO_4$ pH 7.2, 0.1 mM $MnCl_2$, 5% sucrose, 10 mM DTT and eluted with the same buffer. The samples were applied to a Econo-Pac HTP column (BioRad, Hercules, Calif., U.S.A.) that was equilibrated with 10 mM $NaH_2PO_4$ pH 7.2, 0.1 mM $MnCl_2$, 5% sucrose, 10 mM DTT. The column was washed with 10 mM $NaH_2PO_4$ pH 6.8, 0.1 mM $MnCl_2$, 5% sucrose, 10 mM DTT and then eluted with a linear gradient from 10 mM $NaH_2PO_4$ pH 6.8, 0.1 mM $MnCl_2$, 5% sucrose, 10 mM DTT to 400 mM $NaH_2PO_4$ pH 6.8, 0.1 mM $MnCl_2$, 5% sucrose, 10 mM DTT. The samples having oxaloacetate hydrolase activity were used for SDS-PAGE.

Example 2

Protein Sequence Determination of Fragments of the Oxaloacetate Hydrolase

The purified oxaloacetate hydrolase of example 1 was subjected to SDS-PAGE gel electrophoresis on a 12.5% gel using standard methods (Laemmli, U. K., Cleavage of structural proteins during the assembly of the head of bacteriophage T4, *Nature* 227: 680–685 (1970)). The proteins were blotted onto a PVDF membrane by electroblotting, and the membrane was stained with Coomassie brilliant blue R-250 as described by Plough et al (Plough M, Jensen A. L. and Barkholt V., *Anal. Biochem.* 181: 33–39 (1989)). 4 protein bands in the range of an apparent molecular weight of 38 to 40 kD were excised and applied for amino terminal sequencing using a Procise –494 protein sequencer from PerkinElmer—Applied Biosystems, Norwalk, Conn., U.S.A. following the manufacturer's instructions. The following sequences were obtained:

```
1.   MKVDTPDSASTISMTN   (SEQ ID NO: 3)
2.   TNTITITVEQDGIYE    (SEQ ID NO: 4)
3.   VEQDGIYEIN         (SEQ ID NO: 5)
4.   GARQEPVVNLNMVTG.   (SEQ ID NO: 6)
```

Example 3

Cloning of the Gene Encoding the Oxaloacetate Hydrolase

The protein sequences determined in example 2 were used for database searches, and an *Aspergillus niger* EST sequence was retrieved (EMBL, T82752, AN752). This EST encoded a protein sequence that could be aligned to the four sequences from example 2 with 100% identity. The EST sequence was used to design the following PCR primers:

```
Oxalac EST    5' AAA GTT GAT ACC CCC GAT TCT 3'     (SEQ ID NO: 7)
sense:

Oxalac EST    5' ATG GCA ATA CGG GGA CAG ACC 3'.    (SEQ ID NO: 8)
antisense:
```

These primers were used to amplify DNA from *A. niger* BO 1 prepared essentially as described by Leach et. al. (J. Leach, D. B. Finkelstein and J. A. Rambosek, *Fungal Gent. Newsl.* 33: 32–33 (1986)) using amplitaq taq polymerase from PerkinElmer (Norwalk, Conn., U.S.A.) following the manufacturer's instructions. The PCR reaction was run in an MJ PCT 150 capillary PCR cycler (M. J. research, Watertown, Mass., U.S.A. in a volume of 10 microliters running 30 cycles with a denaturation temperature of 94° C. for 10 sec, an annealing temperature of 55° C. for 10 sec and an elongation temperature of 72° C. for 30 sec with a temperature gradient from denaturation to annealing of –0.5° C./sec.

The obtained 219 bp fragment was ligated into the pCR II vector (Invitrogen, Carlsbad, Calif., U.S.A.) following the manufacturer's instructions and transformed into *Escherichia coli* DH 5α as described by Sambrook (J. Sambrook et al., Molecular Cloning, A Laboratory Manual, second edition, Cold Spring Harbor Laboratory Press (1989)). A clone containing an insert of the expected size was sequenced using the primers:

```
                                        (SEQ ID NO: 9)
M13 reverse      5' CAG GAA ACA GCT ATG AC 3'.
primer:

(SEQ ID NO: 10)
M13 Forward (-20)  5' GTA AAA CGA CGG CCA G 3'.
primer:
```

The DNA sequence analysis was made using an ABI PRISM 377 DNA Sequencer together with the ABI PRISM BigDye Terminator Cycle Sequencing Ready Reaction Kit (PerkinElmer Applied Biosystems, Foster city, Calif., U.S.A.) following the manufacturer's recommendations. The sequences confirmed the fragment to be the desired sequence.

A restriction map was established by Southern blot analysis using the 219 bp insert as a probe following the protocols of Sambrook et al. From this restriction map it was concluded that the gene was located on a 5 kb Bgl II fragment.

The gene was then cloned by inverse PCR: Genomic DNA from *A. niger* BO 1 was digested with Bgl II, and fragments ranging from 4 kb to 6 kb were recovered from an agarose gel. The DNA was ligated using T4 DNA ligase at 16° C. This ligation mixture was used as template in a PCR reaction using the following primers:

```
                                            (SEQ ID NO: 11)
OXEST1    5' GAC GGT CTG TCG CCG TAT TGC 3'

(SEQ ID NO: 12)
OXEST2    5' GGA AGC AGA ATC GGG GGT ATC 3'.
```

The Expand high fidelity polymerase (Boehringer Mannheim, Mannheim, Germany) was used for the amplification following the manufacturer's recommendations. The MgCl$_2$ concentration in the reaction was 1 mM. Otherwise the conditions were as above. A 5 kb fragment was generated. This fragment was digested with Bgl II, and the digested fragment was ligated to pUC 19 (C. Yanisch-Perron et al., *Gene* 33: 103–119 (1985)) digested with BamH I and Hinc II. The ligation mixture was transformed into *E. coli* DH 5α. Colonies having insert sizes of 1.3 kb and 3.7 kb were found. One colony of each class were sequenced using the M13 reverse primer and the M13 Forward (–20) primer. In this way the Bgl II neighboring sequences were determined, and the following primers were designed to PCR amplify the 5 kb Bgl II fragment:

```
Flank 1: 5' GCG GCC GCG CGC CAA TAA CGT CCG ATT C 3'    (SEQ ID NO: 13)

Flank 2: 5' GCG GCC GCC TAC AAA TAC ATT GAC CTC CC 3'.  (SEQ ID NO: 14)
```

These primers were used to amplify genomic *A. niger* BO 1 DNA using the same PCR conditions as for the inverse PCR. The generated 5 kb fragment was ligated into pCR II to form pHP I. The oxaloacetate hydrolase gene was sequenced using pHP I as template with the following primers:

```
Oxalac EST sense:       5' AAA GTT GAT ACC CCC GAT TCT 3'              (SEQ ID NO: 15)

Oxalac EST antisense:   5' ATG GCA ATA CGG CGA CAG ACC 3'              (SEQ ID NO: 16)

OXEST 1:                5' GAC GGT CTG TCG CCG TAT TGC 3'              (SEQ ID NO: 17)

OXEST 2:                5' GGA AGC AGA ATC GGG GGT ATC 3'              (SEQ ID NO: 18)

OXEST 3:                5' GCC GGA GTC GCG GGA TTC CAC 3'              (SEQ ID NO: 19)

OXEST 4:                5' GGC GGA CTA TGA TTT GTG CC 3'               (SEQ ID NO: 20)

OX5:                    5' TGA TGG TCG CCC GTT CCG TT 3'               (SEQ ID NO: 21)

OX6:                    5' TGC CAT TCA ATT TTC TTG GCC 3'              (SEQ ID NO: 22)

OX7:                    5' TGA TCT TCG ATG TGG AAT CCC 3'              (SEQ ID NO: 23)

OX8:                    5' GAT GGC GTC GAT TGA CCA TTT 3'              (SEQ ID NO: 24)

OX9:                    5' GGA GAT GGG TTT GCT AAT GGT GTT 3'          (SEQ ID NO: 25)

OX10:                   5' TTA GCA AAC CCA TCT CCA CC 3'               (SEQ ID NO: 26)

OX11:                   5' CGA ATT ACT GGT CAT TAG CCC 3'              (SEQ ID NO: 27)

OX12:                   5' CGA GAG AAG TAT TCT AGA CCC 3'              (SEQ ID NO: 28)

OX13:                   5' TGA CTG TCG ATC AGG GTG TT 3'               (SEQ ID NO: 29)

OX14:                   5' GTG TGC GGA TTG ATG GAC TC 3'               (SEQ ID NO: 30)

OX15:                   5' CAA CCC AAC TCA ACA ACT CT 3'               (SEQ ID NO: 31)

FLANKE1:                5' GCG GCC GCG CGC CAA TAA CGT CCG ATT C 3'    (SEQ ID NO: 32)

FLANKE2:                5' GCG GCC GCC TAC AAA TAC ATT GAC CTC CC 3'   (SEQ ID NO: 33)
```

The DNA sequence is shown in SEQ ID NO: 1. The sequence was analyzed for coding sequence and for the presence of introns using the computer software Netgene 2 (S. M. Hebsgaard, P. G. Korning, N. Tolstrup, J. Engelbrecht, P. Rouze, S. Brunak (*Nucleic Acids Research* 24: 3439–3452 (1996)) suggested the existence of 3 exons (see annotations to SEQ ID NO: 1). The 341 residue protein sequence deduced from these 3 introns is shown in SEQ ID NO: 2.

Data base searches using this protein sequence (oah) as the query sequence revealed sequence homology to Isocitrate lyase from *Aspergillus nidulans* (Swiss prot P28298) and *Neurospora crassa* (Swiss prot P28299) as well as carboxyvinyl-carboxyphosphonate phosphorylmutase from *Streptomyces hygroscopicus* (Swiss prot P11435) and a hypothetical protein from *Bacillus subtilis* (Swiss prot P54528).

|        | Oah   | P28298 | P28299 | P11435 | P54528 |
|--------|-------|--------|--------|--------|--------|
| oah    | 100.0 | 20.2   | 21.0   | 29.7   | 29.1   |
| P28298 | 20.2  | 100.0  | 74.3   | 17.6   | 19.3   |
| P28299 | 21.0  | 74.3   | 100.0  | 18.1   | 18.6   |
| P11435 | 29.7  | 17.6   | 18.1   | 100.0  | 36.5   |
| P54528 | 29.1  | 19.3   | 18.6   | 36.5   | 100.0  |

A strain of *E. coli* harboring the plasmid pHP1 was deposited as DSM 12660.

Example 4

Figure 2:
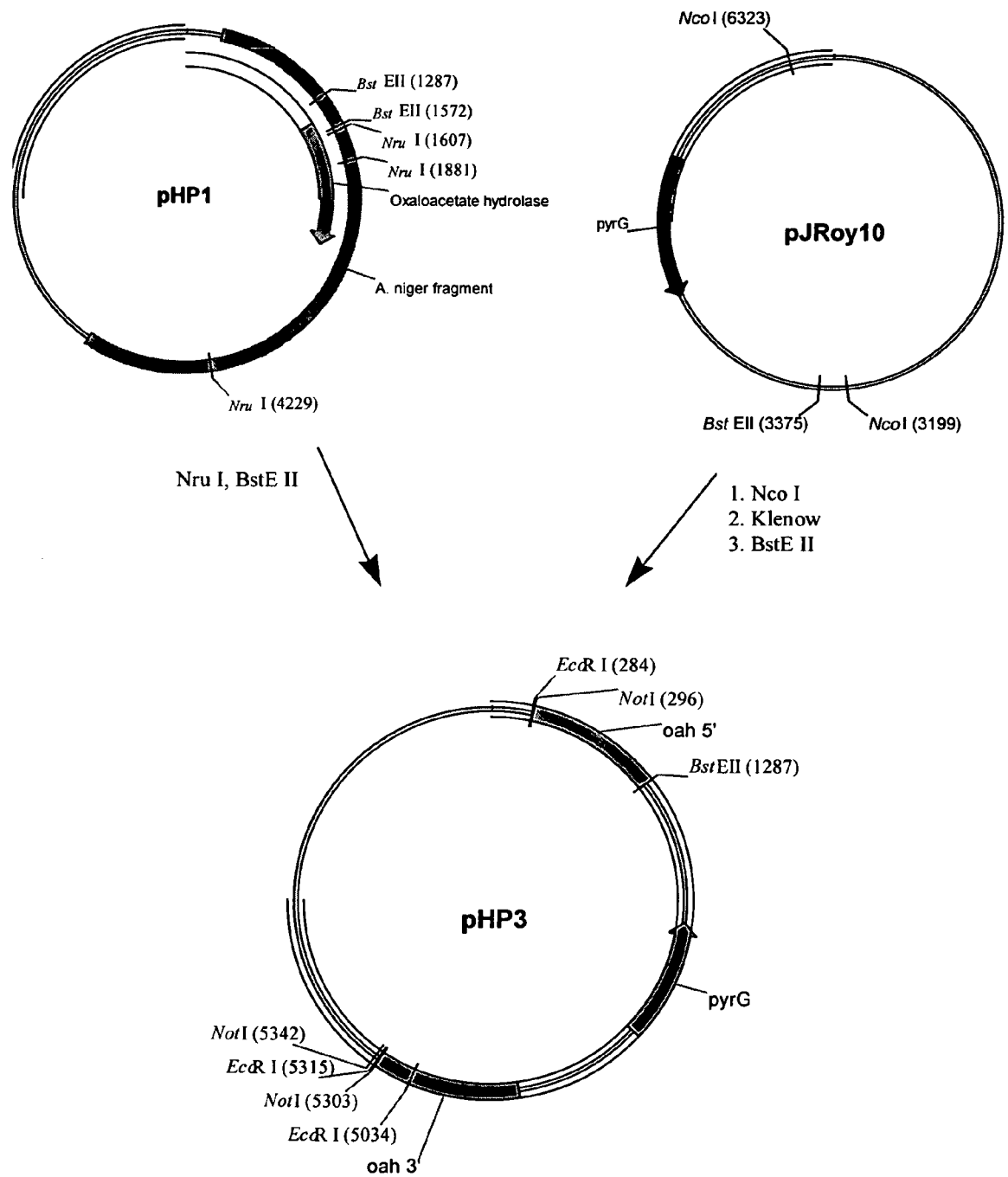
FIG. 2 shows the construction of plasmid pHP3 described in Example 4.

Disruption of the Oxaloacetate Hydrolase Gene pHP I was digested with Nru I and BstE II and the 6.6 kb fragment was isolated. A plasmid harboring the *Aspergillus niger* pyrG gene, pJRoy 10 (FIG. 1), was digested with Nco I, and the 5' recessive ends were then filled in with the Klenow fragment of DNA polymerase I, and then digested with BstE II. The 2948 bp fragment was isolated and ligated to the pHP I fragment. The ligation mixture was used to transform *E. coli* DH5α. A colony harboring the desired plasmid was identified, and the plasmid was termed pHP 3 (FIG. 2). A strain of *E. coli* harboring the plasmid pHP3 was deposited as DSM 12661.

The pyrG deficient *A. niger* BO 1 derivative JRoy3 (BO1 was rendered pyrG negative by transforming with a deletion fragment of the pyrG gene region and selecting on FOA) was transformed with the 5 kb EcoR I-Not I fragment of pHP 3 using the method described in the EP patent EP 0 531 372 B1. 275 transformants were reisolated twice and then grown up in 96 well microtiter dishes at 34° C., pH 6.0 for 48 hr in the medium glucose 20 g/L, NaNO$_3$ 15 g/L, KH$_2$PO$_4$ 1.5 g/L, MgSO$_4$, 7H$_2$O 1 g/L, NaCl 1 g/L, CaCl$_2$, 2H$_2$O 0.1 g/L, tracer solution 0.5 ml/L. Tracer solution: ZnSO$_4$, 7H$_2$O 14.3 g/L, CuSO$_4$, 5H$_2$O 2.5 g/L, NiCl$_2$, 6H$_2$O 0.5 g/L, FeSO$_4$, 7H$_2$O 13.8 g/L, MnCl$_2$ 6 g/L. The supernatants were assayed for oxalate using the Sigma (St. Louis, Mo., U.S.A.) oxalate (cat no 591-C) kit. Eight transformants were found not to produce oxalate. 6 of those were subjected to Southern blot analysis together with 2 oxalate producing transformants, BO 1 and JRoy 3 as positive controls. The 219 bp EST PCR fragment described in example 3 was used as probe. A separate blot of the same samples was probed with the Nco I-BstE II fragment of pJRoy 10. The Southern blots revealed that the 6 oxalate negative strains were disrupted in the oxaloacetate gene, whereas the positive controls contained intact oxaloacetate genes.

Example 5

Fermentation of an Oxalate Negative Strain

One of the oxalate negative strains was grown in a batch fermenter equipped with stirring, temperature control, pH control and aeration. The medium was glucose 16 g/L, $(NH_4)_2SO_4$ 7.5 g/L, $KH_2PO_4$ 1.5 g/L, $MgSO_4$, $7H_2O$ 1 g/L, NaCl 1 g/L, $CaCl_2$, $2H_2O$ 0.1 g/L, trace solution 0.5 ml/L. Trace solution: $ZnSO_4$, $7H_2O$ 14.3 g/L, $CuSO_4$, $5H_2O$ 2.5 g/L, $NiCl_2$, $6H_2O$ 0.5 g/L, $FeSO_4$, $7H_2O$ 13.8 g/L, $MnCl_2$ 6 g/L. The pH was 2.5 until the biomass had reached a concentration of 0.5 g/L. At this point the pH was shifted to pH 6.0. The fermentation broth was analyzed for oxalate, citrate, pyruvate, succinate, acetate, glycerol, ethanol and glucose (Nissen, T. L., U. Schulze, J. Nielsen, and J. Villadsen, Flux distributions in anaerobic, glucose-limited continuous cultures of *Saccharomyces cerevisiae, Microbiol.* 143: 203–218 (1997)). Of bi-products only citrate, pyruvate, succinate and glycerol could be detected and the maximum concentrations of these bi-products were 0.74 g/L, 0.18 g/L, 0.14 g/L and 0.13 g/L respectively. The biomass yield on glucose was 0.58 g/g and the specific growth rate was 0.23 $h^{-1}$.

Deposit of Biological Material

The following biological material has been deposited under the terms of the Budapest Treaty with the DSMZ-Deutsche Sammlung von Mikroorganismen und Zellkulturen GmbH, Mascheroder Weg 1b, D-38124 Braunschweig, Germany, and given the following accession numbers:

| Depositor's ref: | Accession Number | Date of Deposit |
| --- | --- | --- |
| NN049454 | DSM 12660 | Feb. 3, 1999 |
| NN049455 | DSM 12661 | Feb. 3, 1999 |
| NN049047 | DSM 12665 | Feb. 3, 1999 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. A method for producing citric acid, comprising
 (a) culturing a mutant of a parent cell, wherein the mutant produces less oxaloacetate hydrolase than the parent cell, wherein the oxaloacetate hydrolase
  (i) has an amino acid sequence that has at least 90% identity with amino acids 1-341 of SEQ ID NO:2;
  (ii) is encoded by a nucleic acid sequence having at least 90% homology with the cDNA sequence of SEQ ID NO: 1; and/or
  (iii) is encoded by a nucleic acid sequence which hybridizes under high stringency conditions with the nucleic acid sequence of SEQ ID NO: 1, the cDNA sequence of SEQ ID NO: 1, the complete complementary strand of SEQ ID NO: 1, and/or the complete complementary strand of the cDNA sequence of SEQ ID NO: 1, wherein the high stringency conditions are defined as prehybridization and hybridization at 42° C. in 5×SSPE, 0.3% SDS, 200 micrograms/ml sheared and denatured salmon sperm DNA, and 50% formamide, followed by washing three times for 15 minutes using 2×SSC, 0.2% SDS at 65° C.; and
 (b) recovering the citric acid.

2. The method of claim 1, wherein the oxaloacetate hydrolase has an amino acid sequence that has at least 90% identity with amino acids 1–341 of SEQ ID NO: 2.

3. The method of claim 2, wherein the oxaloacetate hydrolase has an amino acid sequence that has at least 95% identity with amino acids 1–341 of SEQ ID NO: 2.

4. The method of claim 3, wherein the oxaloacetate hydrolase has an amino acid sequence that has at least 97% identity with amino acids 1–341 of SEQ ID NO: 2.

5. The method of claim 1, wherein the oxaloacetate hydrolase has an amino acid sequence which comprises SEQ ID NO: 2 or a fragment of SEQ ID NO: 2 that has oxaloacetate hydrolase activity.

6. The method of claim 1, wherein the oxaloacetate hydrolase has the amino acid sequence of SEQ IDNO: 2.

7. The method of claim 1, wherein the parent cell comprises the nucleic acid sequence of SEQ IDNO: 1.

8. The method of claim 1, wherein the parent cell comprises the cDNA sequence of SEQ ID NO: 1.

9. The method of claim 1, wherein the oxaloacetate hydrolase is encoded by a nucleic acid sequence that hybridizes under said high stringency conditions with the nucleic acid sequence of SEQ ID NO: 1, the cDNA sequence of SEQ ID NO: 1, the complete complementary strand of SEQ ID NO: 1, and/or the complete complementary strand of the cDNA sequence of SEQ ID NO: 1.

10. The method of claim 1, wherein the parent cell is a filamentous fungal cell.

11. The method of claim 10, wherein the parent cell is a cell of *Acremonium, Aspergillus, Aureobasidium, Cryptococcus, Filibasidium, Fusarium, Gibberella, Humicola, Magnaporthe, Mucor, Myceliophthora, Myrothecium, Neocallimastix, Neurospora, Paecilomyces, Penicillium, Piromyces, Schizophyllum, Talaromyces, Thermoascus, Thielavia, Tolypocladium,* or *Trichoderma* strain.

12. The method of claim 11, wherein the parent cell is a cell of *Aspergillus*.

13. The method of claim 12, wherein the parent cell is a cell of *A. niger*.

14. The method of claim 1, wherein the mutant produces at least about 25% less of the oxaloacetate hydrolase than the parent cell when cultured under identical conditions.

15. The method of claim 14, wherein the mutant produces no oxaloacetate hydrolase.

* * * * *